(12) United States Patent
Tian et al.

(10) Patent No.: US 12,004,886 B2
(45) Date of Patent: Jun. 11, 2024

(54) SECOND NEAR-INFRARED WINDOW / FIRST NEAR-INFRARED WINDOW DUAL-MODE FLUORESCENCE TOMOGRAPHY SYSTEM AND METHOD

(71) Applicant: INSTITUTE OF AUTOMATION, CHINESE ACADEMY OF SCIENCES, Beijing (CN)

(72) Inventors: Jie Tian, Beijing (CN); Zhenhua Hu, Beijing (CN); Meishan Cai, Beijing (CN); Caiguang Cao, Beijing (CN)

(73) Assignee: INSTITUTE OF AUTOMATION, CHINESE ACADEMY OF SCIENCES, Beijing (CN)

( * ) Notice: Subject to any disclaimer, the term of this patent is extended or adjusted under 35 U.S.C. 154(b) by 687 days.

(21) Appl. No.: 16/845,267

(22) Filed: Apr. 10, 2020

(65) Prior Publication Data

US 2021/0000437 A1    Jan. 7, 2021

(30) Foreign Application Priority Data

Jul. 4, 2019  (CN) .......................... 201910599396.9

(51) Int. Cl.
*A61B 6/03*      (2006.01)
*A61B 5/00*      (2006.01)
(Continued)

(52) U.S. Cl.
CPC ............ *A61B 6/032* (2013.01); *A61B 5/0035* (2013.01); *A61B 5/0071* (2013.01);
(Continued)

(58) Field of Classification Search
CPC ... A61B 6/5247; A61B 5/0035; A61B 5/0071; A61B 5/0073; A61B 6/032; A61B 6/508;
(Continued)

(56) References Cited

U.S. PATENT DOCUMENTS 7,401,984 B2 * 7/2008 Pattie ................. A61B 1/00126
385/71
10,064,584 B2 * 9/2018 Yared .................. A61B 5/0064
(Continued)

FOREIGN PATENT DOCUMENTS

CN        109827536 A  *  5/2019
WO   WO-2014019351 A1 *  2/2014 ........... A61B 6/4417

OTHER PUBLICATIONS

Tang, Lu, and Peter X K Song. "Fused Lasso Approach in Regression Coefficients Clustering—Learning Parameter Heterogeneity in Data Integration." Journal of machine learning research : JMLR vol. 17 (2016): 1-7 (Year: 2016).*

*Primary Examiner* — Christopher Koharski
*Assistant Examiner* — Richmond J Van Winter
(74) *Attorney, Agent, or Firm* — Husch Blackwell LLP

(57) ABSTRACT

A second near-infrared window/first near-infrared window dual-mode fluorescence tomography system having a lighting module, an excitation module, a second near-infrared window collection module, a first near-infrared window collection module, a CT imaging module and a central control module. The central control module is configured to reconstruct second near-infrared window three-dimensional and tomographic images and first near-infrared window three-dimensional and tomographic images based on the white light images, the second near-infrared window fluorescent images, the first near-infrared window fluorescent images, and the CT images. The reconstructed three-dimensional space tumor signal has depth characteristics, which is closer to the real distribution of tumors, such that the reconstruction position is more accurate. The three-dimensional shape of the tumor is displayed intuitively and clearly at any angle with the usage of image display unit.

6 Claims, 6 Drawing Sheets

(51) Int. Cl.

| | |
|---|---|
| *A61B 6/00* | (2024.01) |
| *A61B 6/50* | (2024.01) |
| *G06T 7/00* | (2017.01) |
| *G06T 11/00* | (2006.01) |
| *G06V 10/141* | (2022.01) |

(52) U.S. Cl.
CPC ............ *A61B 5/0073* (2013.01); *A61B 6/508* (2013.01); *A61B 6/5247* (2013.01); *A61B 6/54* (2013.01); *A61B 6/56* (2013.01); *G06T 7/0012* (2013.01); *G06T 11/001* (2013.01); *G06V 10/141* (2022.01); *A61B 2503/40* (2013.01); *A61B 2562/0233* (2013.01); *G06T 2207/10064* (2013.01); *G06T 2207/10081* (2013.01); *G06T 2207/10116* (2013.01); *G06T 2207/30004* (2013.01)

(58) Field of Classification Search
CPC ......... A61B 6/54; A61B 6/56; A61B 2503/40; A61B 2562/0233; A61B 2503/42; G06T 7/0012; G06T 11/001; G06T 2207/10064; G06T 2207/10081; G06T 2207/10116; G06T 2207/30004; G06T 11/006; G06V 10/141; G06V 2201/03
See application file for complete search history.

(56) References Cited

U.S. PATENT DOCUMENTS 10,108,008 B2 * 10/2018 Fukuyama ......... G02B 27/0068
2012/0123205 A1 * 5/2012 Nie ..................... A61B 5/0084
600/109
2015/0289829 A1 * 10/2015 Yamada ................. A61B 6/56
378/209

* cited by examiner

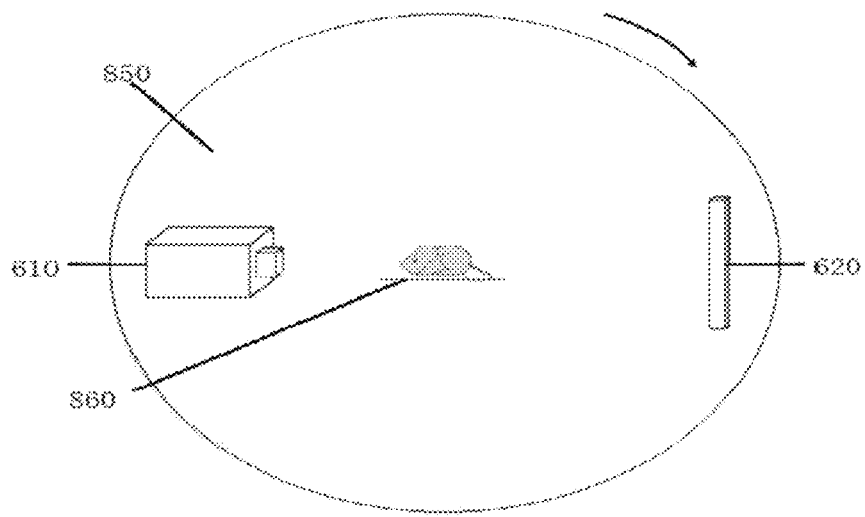

FIG. 4

| THE WHITE LIGHT EMITTING DEVICE IS TURNED ON, AND CONTROL SIGNALS ARE OUTPUT, BY THE SIGNAL CONTROL UNIT OF THE CENTRAL CONTROL MODULE, TO A FIRST NEAR-INFRARED WINDOW COLLECTION CAMERA AND A SECOND NEAR-INFRARED WINDOW COLLECTION CAMERA TO CAUSE THE CAMERAS TO COLLECT THE WHITE LIGHT IMAGES | S100 |

| THE WHITE LIGHT EMITTING DEVICE IS TURNED OFF, THE LASER IS TURNED ON TO OUTPUT THE EXCITATION LIGHT, AND CONTROL SIGNALS ARE OUTPUT, BY THE SIGNAL CONTROL UNIT OF THE CENTRAL CONTROL MODULE, TO THE FIRST NEAR-INFRARED WINDOW FLUORESCENT CAMERA AND THE SECOND NEAR-INFRARED WINDOW FLUORESCENT CAMERA TO CAUSE THE CAMERAS TO COLLECT THE FLUORESCENT IMAGES | S200 |

| THE LASER IS TURNED OFF, AND A CONTROL SIGNAL IS OUTPUT, BY THE SIGNAL CONTROL UNIT OF THE CENTRAL CONTROL MODULE, TO THE CT IMAGING MODULE TO COLLECT THE CT IMAGES | S300 |

| DE-NOISING AND ENHANCING PRE-PROCESS IS PERFORMED, BY THE IMAGE PROCESSING UNIT OF THE CENTRAL CONTROL MODULE, ON THE WHITE LIGHT IMAGES, THE FLUORESCENT IMAGES, AND THE CT IMAGES COLLECTED IN STEPS S100, S200 AND S300 | S400 |

| THE FLUORESCENT IMAGES ARE REGISTERED, BY THE THREE-DIMENSIONAL RECONSTRUCTION UNIT OF THE CENTRAL CONTROL MODULE, TO THE CT IMAGES ACCORDING TO THE WHITE LIGHT IMAGES, THE THREE-DIMENSIONAL IMAGES OF THE TUMOR IN THE BODY OF THE MOUSE ARE OBTAINED BY COMBINING THE FLUORESCENCE DISTRIBUTION, LIGHT INTENSITIES AND OTHER INFORMATION, AND THE THREE-DIMENSIONAL RECONSTRUCTION OF NEAR-INFRARED FLUORESCENCE TUMOR THREE-DIMENSIONAL RECONSTRUCTION SYSTEM IS COMPLETED | S500 |

FIG. 5

SECOND NEAR-INFRARED WINDOW / FIRST NEAR-INFRARED WINDOW DUAL-MODE FLUORESCENCE TOMOGRAPHY SYSTEM AND METHOD

CROSS-REFERENCE TO RELATED APPLICATION(S)

This application claims priority to Chinese Patent Application No. 201910599396.9, filed with the Chinese Patent Office on Jul. 4, 2019 and entitled "SECOND NEAR-INFRARED WINDOW/FIRST NEAR-INFRARED WINDOW DUAL-MODE FLUORESCENCE TOMOGRAPHY SYSTEM AND METHOD", which is incorporated herein by reference entirely.

TECHNICAL FIELD

The present disclosure belongs to the field of fluorescence imaging, and particularly relates to a second near-infrared window/first near-infrared window dual-mode fluorescence tomography system and method.

BACKGROUND

Cancer is one of the major diseases that threaten the health of human and has a high mortality rate. "Early detection and early treatment" is the key measure to reduce the mortality of cancer patients and improve their quality of life. However, traditional tumor detection methods such as CT (abbreviations for Computed Tomography, i.e., Computerized Tomography), MRI (abbreviation for Magnetic Resonance Imaging) and ultrasound cannot accurately detect early small tumors. With the development of medical imaging technology, optical molecular imaging technology is expected to become a new generation of imaging models for early high-precision detection of cancer, which is of great value to the clinic.

Optical molecular imaging technology mainly comprises two-dimensional optical imaging technology and three-dimensional optical tomography technology. Three-dimensional molecular imaging can locate the spatial position of the tumor in the living body, which makes up for the defect of depth information loss of the two-dimensional optical imaging technology, and has more clinical application value. The currently fast-developing three-dimensional tomography technology is fluorescence molecular tomography in the near-infrared window. By injecting targeted fluorescent probes, using lasers to excite the probes, collecting emitted light, then combining structural images, non-invasive, non-intrusive lesion detection and spatial positioning can be achieved. However, it has the defects of poor imaging quality and inability to provide a good analytical basis for diagnosis.

SUMMARY

In order to solve the above problems in the prior art, that is, poor imaging quality, low positioning accuracy, and inability to provide a good analytical basis for diagnosis, the first aspect of the present disclosure provides a second near-infrared window/first near-infrared window dual-mode fluorescence tomography system, comprising:
 a lighting module configured to irradiate a mouse with a white light and collect white light images;
 an excitation module configured to irradiate a tumor region of the mouse with a second near-infrared window excitation light and a first near-infrared window excitation light such that fluorescent dye in the tumor region emits fluorescence;
 a second near-infrared window collection module configured to collect white light images in the second near-infrared window and second near-infrared window fluorescent images formed by the fluorescence emitted by the fluorescent dye in the tumor region;
 a first near-infrared window collection module configured to collect white light images in the first near-infrared window and first near-infrared window fluorescent images formed by the fluorescence emitted by the fluorescent dye in the tumor region;
 a CT imaging module configured to irradiate the mouse and generate CT images for the mouse; and
 a central control module configured to reconstruct second near-infrared window three-dimensional and tomographic images and first near-infrared window three-dimensional and tomographic images based on the white light images, the second near-infrared window fluorescent images, the first near-infrared window fluorescent images, and the CT images, wherein
 the white light images are used to register the second near-infrared window fluorescent images to the CT images and to register the first near-infrared window fluorescent images to the CT images;
 the second near-infrared window fluorescent images are used to reconstruct a second near-infrared window fluorescent light source distribution in a body of the mouse; and
 the first near-infrared window fluorescent images are used to reconstruct a first near-infrared window fluorescent light source distribution in the body of the mouse.

In some preferred embodiments, the lighting module comprises a white light emitting device, a white light conducting device and a white light beam expanding device, which are sequentially connected in an optical path, wherein
 the white light emitting device is configured to emit the white light, and the white light emitting device has an adjustable luminous intensity;
 the white light conducting device is configured to conduct a white light signal emitted by the white light emitting device to an imaging range of the mouse; and
 the white light beam expanding device is disposed near the imaging range, and the white light beam expanding device is configured to expand the white light to be irradiated to the mouse to produce a uniform lighting effect.

In some preferred embodiments, the excitation module comprises a laser, an adapter device, an excitation light conducting device, and an excitation light beam expanding device, which are sequentially connected in an optical path, wherein
 the laser is configured to emit the second near-infrared window excitation light and the first near-infrared window excitation light with tunable wavelengths;
 the excitation light conducting device is configured to conduct the excitation lights;
 the adapter device is configured to conduct the excitation lights emitted by the laser to the excitation light conducting device; and
 the excitation light beam expanding device is configured to diverge the excitation lights.

In some preferred embodiments, the second near-infrared window collection module comprises a second near-infrared window transmission increasing lens, a second near-infrared window adapter ring and a second near-infrared window camera, which are sequentially connected in an optical path, and the second near-infrared window collection module further comprises a second near-infrared window bandpass filter disposed between the second near-infrared window transmission increasing lens and the second near-infrared window camera, wherein the second near-infrared window camera is configured to collect the second near-infrared window fluorescent images and the white light images;

the second near-infrared window transmission increasing lens is configured to increase transmission of the second near-infrared window fluorescence;

the second near-infrared window adapter ring is configured to connect the second near-infrared window camera and the second near-infrared window transmission increasing lens; and the second near-infrared window bandpass filter is configured to filter out stray light outside the second near-infrared window.

In some preferred embodiments, the first near-infrared window collection module comprises a zoom lens, a first near-infrared window adapter ring, and a first near-infrared window camera, which are sequentially connected in an optical path, and the first near-infrared window collection module further comprises a first near-infrared window bandpass filter disposed between the zoom lens and the first near-infrared window camera, wherein the first near-infrared window camera is configured to collect the first near-infrared window fluorescent images and the white light images;

the zoom lens is configured to adjust a size of an imaging area;

the first near-infrared window adapter ring is configured to connect the first near-infrared window camera and the zoom lens; and the first near-infrared window bandpass filter is configured to filter out stray light outside the first near-infrared window.

In some preferred embodiments, the CT imaging module comprises:

an X-ray emitter configured to emit X-rays to irradiate the mouse;

an X-ray detector configured to receive the X-rays, generate the CT images, and perform the collection;

a CT data cable configured to send the generated CT images to the central control module; and a CT power cable configured to power the CT imaging module.

In some preferred embodiments, the system further comprises a rack, a turntable, and a mobile station, wherein the turntable is mounted on the rack in a manner capable of rotating in a vertical plane, and the turntable is configured to fix the lighting module, the excitation module, the second near-infrared window collection module, the first near-infrared window collection module and the CT imaging module; and the mobile station is configured to fix the mouse, and the mobile station is movable in both a horizontal direction and a vertical direction.

In some preferred embodiments, the central control module comprises:

a signal control unit configured to control the lighting module, the excitation module, the second near-infrared window collection module, the first near-infrared window collection module, and the CT imaging module, respectively;

a data reading unit configured to read the white light images, the second near-infrared window fluorescent images, the first near-infrared window fluorescent images, and the CT images;

an image processing unit configured to pre-process the white light images, the second near-infrared window fluorescent images, the first near-infrared window fluorescent images, and the CT images;

a three-dimensional reconstruction unit configured to register the second near-infrared window fluorescent images to the CT images and register the first near-infrared window fluorescent images to the CT images according to the white light images, and combine the second near-infrared window fluorescent light source distribution, the first near-infrared window fluorescent light source distribution, intensities of the white light images, intensities of the second near-infrared window fluorescent images, and intensities of the first near-infrared window fluorescent images to obtain the second near-infrared window three-dimensional and tomographic images and the first near-infrared window three-dimensional and tomographic images of the tumor region within the body of the mouse.

In some preferred embodiments, the central control module further comprises:

an image display unit configured to display the white light images, the first near-infrared window fluorescent images, the second near-infrared window fluorescent images, the CT images, the second near-infrared window three-dimensional and tomographic images, and the first near-infrared window three-dimensional and tomographic images; and the image display unit is communicatively connected with the signal control unit, the data reading unit, the image processing unit, and the three-dimensional reconstruction unit, respectively.

According to second aspect of this disclosure, a second near-infrared window/first near-infrared window dual-mode fluorescence tomography method is provided. This method is applied to any one of the second near-infrared window/first near-infrared window dual-mode fluorescence tomography system described above, and the second near-infrared window/first near-infrared window dual-mode fluorescence tomography method reconstructs second near-infrared window three-dimensional and tomographic images and first near-infrared window three-dimensional and tomographic images based on Gaussian weighted neighborhood fused Lasso regularization.

Beneficial effects of this disclosure are as follows.

(1) the reconstructed three-dimensional space tumor signal has depth characteristics, which is closer to the real distribution of tumors, such that the reconstruction position is more accurate.

(2) the three-dimensional shape of the tumor is displayed intuitively and clearly at any angle with the usage of image display unit.

BRIEF DESCRIPTION OF THE DRAWINGS

Other features, objects, and advantages of the present application will become more apparent by reading the detailed description of the non-limiting embodiments with reference to the following drawings:

FIG. 4 is an operation principle diagram of a CT imaging module according to an embodiment;

FIG. 5 is a schematic diagram of a second near-infrared window/first near-infrared window dual-mode fluorescence tomography method according to an embodiment;

FIG. 6-1 is a white light image in the second near-infrared window;

FIG. 6-2 is a fluorescent image in the second near-infrared window;

FIG. 6-3 is a white light image in the first near-infrared window;

FIG. 6-4 is a fluorescent image in the first near-infrared window;

FIG. 6-5 is a CT image of a CT slice.

AMONG THE DRAWINGS

Figure 1:
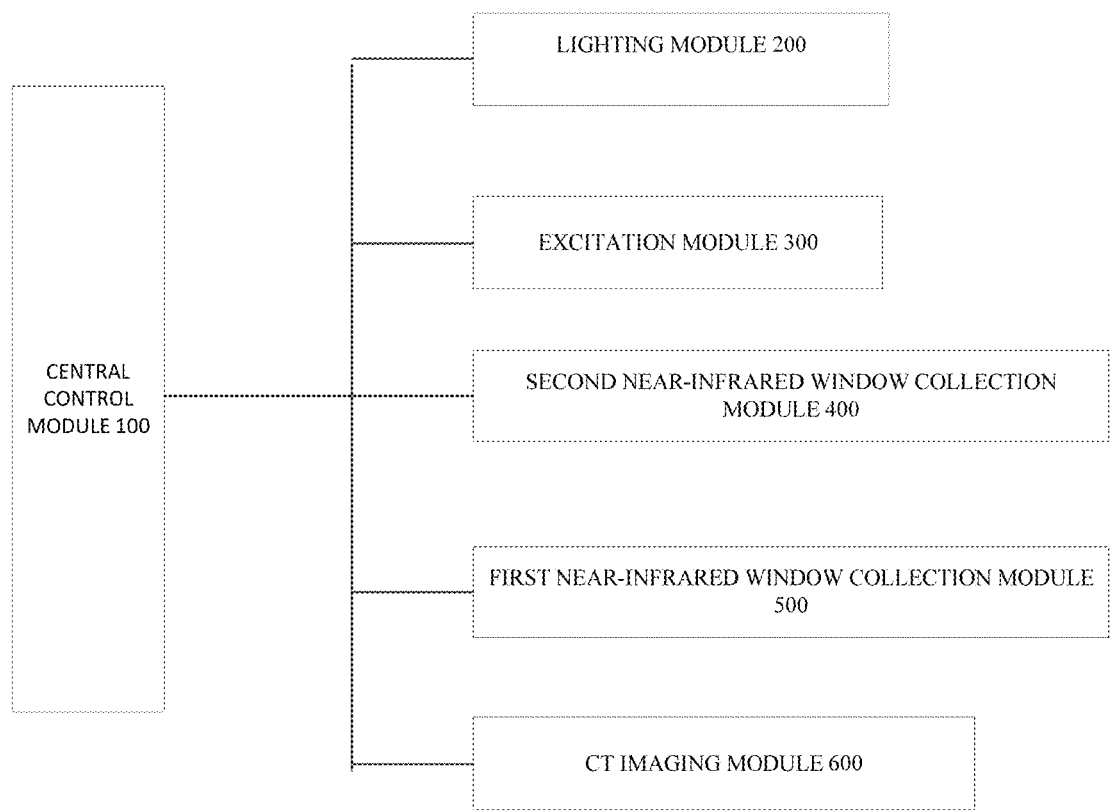
FIG. 1 is a control block diagram of a second near-infrared window/first near-infrared window dual-mode fluorescence tomography system according to an embodiment.

100 Central control module;
200 Lighting module;
300 Excitation module; 310 Laser; 320 Adapter device; 330 Excitation light conducting device; 340 Excitation light beam expanding device;
400 Second near-infrared window collection module; 410 Second near-infrared window camera; 420 Second near-infrared window camera power supply;
500 First near-infrared window collection module; 510 First near-infrared window camera;
600 CT imaging module; 610 X-ray emitter; 620 X-ray detector;
810 Parallel guides; 820 Horizontal movable station; 830 Vertical movable station;
841 First base; 842 Second base; 850 Turntable; 860 Mouse bed.

DETAILED DESCRIPTION

The following describes the present application in detail with reference to the accompanying drawings and embodiments. It may be understood that the specific embodiments described herein are only used to explain the related disclosure, but not to limit the disclosure. It should also be noted that, for the convenience of description, only the parts associated with the related disclosure are shown in the drawings.

It should be noted that the embodiments and features thereof in this application may be combined with each other in the case of no conflict. The application will be described in detail below with reference to the drawings in combination with embodiments.

Figure 2:
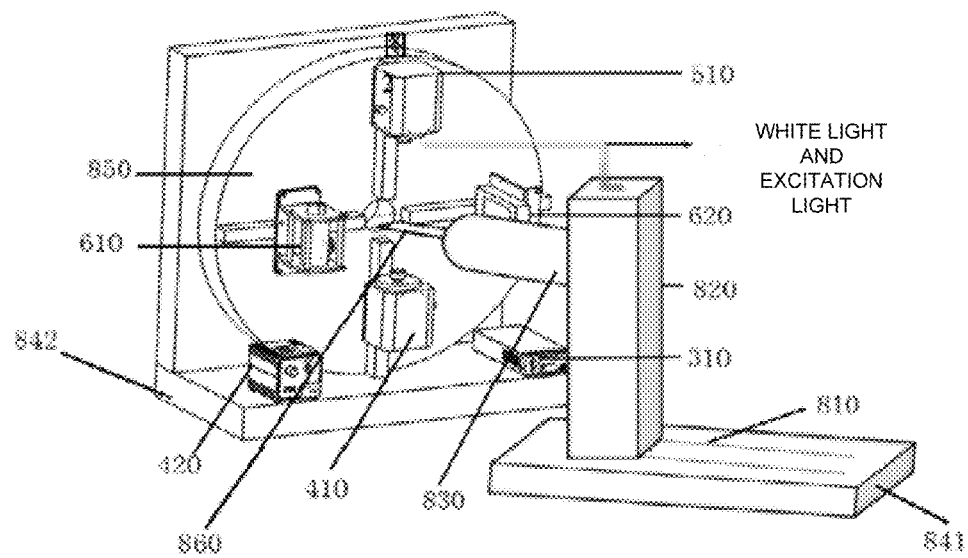
FIG. 2 is a schematic structural diagram of a second near-infrared window/first near-infrared window dual-mode fluorescence tomography system according to an embodiment.
Figure 3:
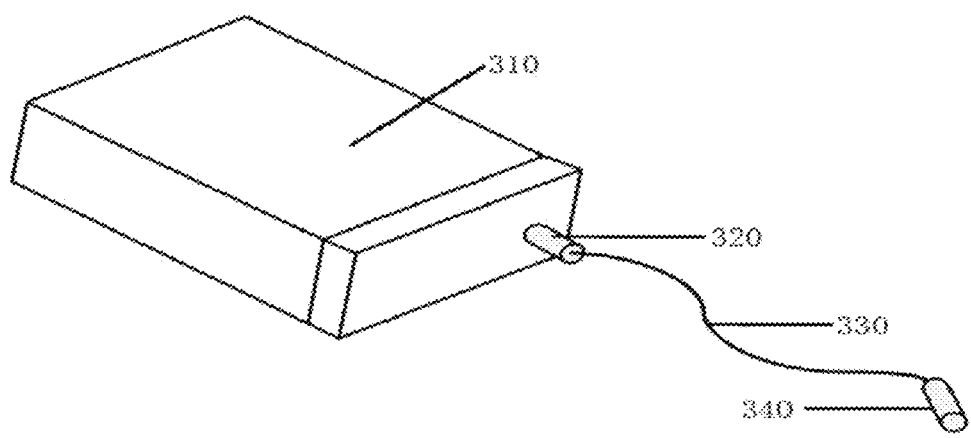
FIG. 3 is a schematic structural diagram of an excitation device according to an embodiment.
Figures 1, 6:
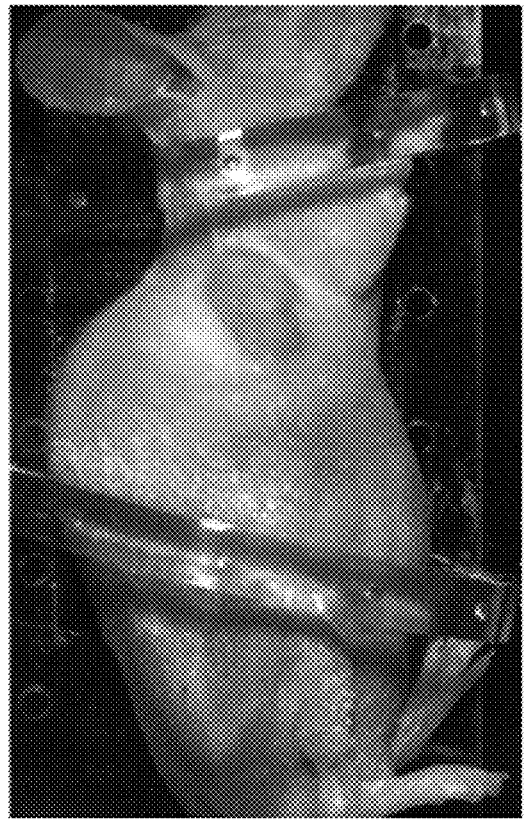
Figures 2, 6:
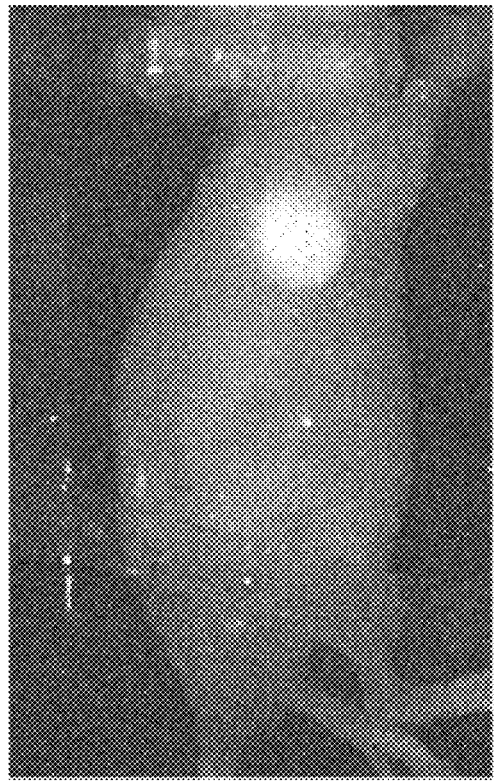
Figures 3, 6:
Figures 4, 6:
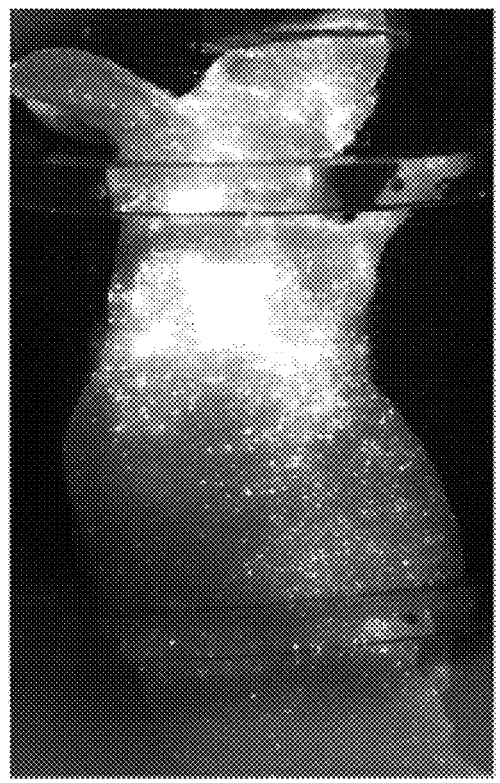
Figures 5, 6:

The first aspect of the embodiment of the present disclosure discloses a second near-infrared window/first near-infrared window dual-mode fluorescence tomography system. Referring to FIGS. 1 and 2, the system comprises:

a lighting module 200 configured to irradiate the mouse with a white light and collect white light images, which can be referred to FIGS. 6-1 and 6-3;

an excitation module 300 configured to irradiate a tumor region of the mouse with a second near-infrared window (NIR-II) excitation light and a first near-infrared window (NIR-I) excitation light such that fluorescent dye in the tumor region emits fluorescence;

a second near-infrared window collection module 400 configured to collect white light images in the second near-infrared window and second near-infrared window fluorescent images formed by the fluorescence emitted by the fluorescent dye of the tumor region, FIG. 6-2 being illustrated as a second near-infrared window fluorescent image;

a first near-infrared window collection module 500 configured to collect white light images in the first near-infrared window and first near-infrared window fluorescent images formed by the fluorescence emitted by the fluorescent dye of the tumor region, FIG. 6-4 being illustrated as a first near-infrared window fluorescent image;

a CT imaging module 600 configured to illuminate the mouse and generate CT images for the mouse, FIG. 6-5 being illustrated as a CT image; and a central control module 100 configured to, based on the white light images, the second near-infrared window fluorescent images, the first near-infrared window fluorescent images, and the CT images, reconstruct second near-infrared window three-dimensional and tomographic images and first near-infrared window three-dimensional and tomographic images, wherein the white light images are used to register the second near-infrared window fluorescence images to the CT images and to register the first near-infrared window fluorescence images to the CT images;

the second near-infrared window fluorescent images are used to reconstruct a second near-infrared window fluorescent light source distribution in the body of the mouse;

the first near-infrared window fluorescent images are used to reconstruct a first near-infrared window fluorescent light sources distribution in the body of the mouse.

With this system, the reconstructed three-dimensional space tumor signal has depth characteristics, which is closer to the real distribution of tumors, such that the reconstruction position is more accurate. The three-dimensional shape of the tumor is displayed intuitively and clearly at any angle with the usage of the image display unit.

In addition, the lighting module comprises a white light emitting device, a white light conducting device and a white light beam expanding device, which are sequentially connected in the optical path, wherein the white light emitting device is configured to emit white light, and the white light emitting device has an adjustable luminous intensity;

the white light conducting device is configured to conduct a white light signal emitted by the white light emitting device to an imaging range of the mouse;

the white light beam expanding device is disposed near the imaging range, and the white light beam expanding device is configured to expand the white light to be irradiated to the mouse to produce a uniform lighting effect.

In addition, a specific structure of the excitation module is shown in FIG. 3, which comprises a laser, an adapter device, an excitation light conducting device and an excitation light beam expanding device, which are sequentially connected in the optical path, wherein:

the laser is configured to emit the second near-infrared window excitation light and the first near-infrared window excitation light with a tunable wavelength;

the excitation light conducting device is configured to conduct the excitation lights;

the adapter device is configured to conduct the excitation lights emitted by the laser to the excitation light conducting device;

the excitation light beam expanding device is configured to diverge the excitation lights.

In addition, the second near-infrared window collection module comprises a second near-infrared window transmission increasing lens, a second near-infrared window adapter ring, and a second near-infrared window camera 410, which are sequentially connected in the optical path. The second near-infrared window collection module further comprises a second near-infrared window bandpass filter disposed between the second near-infrared window transmission increasing lens and the second near-infrared window camera, wherein the second near-infrared window camera is configured to collect the second near-infrared window fluorescent images and the white light images;

the second near-infrared window transmission increasing lens is configured to increase the transmission of the second near-infrared window fluorescence;

the second near-infrared window adapter ring is configured to connect the second near-infrared window camera to the second near-infrared window transmission increasing lens;

the second near-infrared window bandpass filter is configured to filter out stray light outside the second near-infrared window.

Additionally, the second near-infrared window collection module further comprises:

a second near-infrared window camera power supply 420 configured to power the second near-infrared window camera;

a second near-infrared window camera power cable configured to connect the second near-infrared window camera and the second near-infrared window camera power supply;

a second near-infrared window camera data cable configured to connect the second near-infrared window camera and the central control module.

In addition, the first near-infrared window collection module comprises a zoom lens, a first near-infrared window adapter ring and a first near-infrared window camera 510, which are sequentially connected in the optical path, and the first near-infrared window collection module further comprises a first near-infrared window bandpass filter disposed between the zoom lens and the first near-infrared window cameras, wherein the first near-infrared window camera is configured to collect the first near-infrared window fluorescent images and the white light images;

the zoom lens is configured to adjust the size of the imaging area;

the first near-infrared window adapter ring is configured to connect the first near-infrared window camera and the zoom lens;

the first near-infrared window bandpass filter is configured to filter out stray light outside the first near-infrared window.

In addition, the first near-infrared window collection module further comprises:

a first near-infrared window camera power supply configured to power the first near-infrared window camera;

a first near-infrared window camera power cable, configured to connect the first near-infrared window camera and the first near-infrared window camera power supply;

a first near-infrared window camera data cable configured to connect the first near-infrared window camera and the central control module.

Referring to FIG. 4, a specific structure of the CT imaging module comprises:

an X-ray emitter 610 configured to emit X-rays to irradiate the mouse;

a X-ray detector 620 configured to receive the X-rays, generate the CT images, and perform collection;

a CT data cable configured to send the generated CT images to the central control module; and a CT power cable configured to power the CT imaging module.

In addition, the system further comprises a rack, a turntable, and a mobile station, wherein:

the turntable is mounted on the rack in a manner capable of rotating in a vertical plane, and the turntable is configured to fix the lighting module, the excitation module, the second near-infrared window collection module, the first near-infrared window collection module and the CT imaging module;

the mobile station is configured to fix the mouse, and the mobile station is movable in both horizontal direction and vertical direction. Specifically, the rack comprises a first base 841 and a second base 842, and the mouse is fixed to the mobile station by the mouse bed 860. The mobile station comprises a vertical mobile station 830 and a horizontal mobile station 820. The vertical mobile station is mounted (for example, by a ball screw) on the horizontal mobile station in a manner capable of sliding in a vertical direction, and the horizontal mobile station is mounted, by parallel guides 810, on the first base in a manner capable of sliding in a horizontal direction, such that the mouse bed is movable up and down and horizontally. The turntable 850 is rotatably mounted on the second base, and the rotation of the turntable may be driven by a power mechanism such as a servo motor communicatively connected with the central control module. The X-ray emitter, the X-ray detector, the second near-infrared window camera, the first near-infrared window camera, the second near-infrared window camera power supply, and the laser are all mounted on the turntable and rotated with the turntable, so as to realize the circumferential irradiation of the mouse and thus obtaining the corresponding images.

In addition, the central control module comprises:

a signal control unit configured to control the lighting module, the excitation module, the second near-infrared window collection module, the first near-infrared window collection module, and the CT imaging module, respectively;

a data reading unit configured to read the white light images, the second near-infrared window fluorescent images, the first near-infrared window fluorescent images, and the CT images;

an image processing unit configured to pre-process the white light images, the second near-infrared window fluorescent images, the first near-infrared window fluorescent images, and the CT images, and the pre-processing includes either one of image de-noising and image enhancement or combination thereof. Of course, those skilled in the art should know that other image pre-processing methods may also be applied, which are not listed herein;

a three-dimensional reconstruction unit configured to register the second near-infrared window fluorescent images to the CT images and register the first near-infrared window fluorescent images to the CT images according to the white light images, and combine the second near-infrared window fluorescent light source distribution, the first near-infrared window fluorescent light source distribution, the intensities of the white light images, the intensities of the second near-infrared window fluorescent images, and the intensities of the first near-infrared window fluorescent images to obtain the second near-infrared window three-dimensional and tomographic images and the first near-infrared window three-dimensional and tomographic images of the tumor region within the body of the mouse.

In addition, the central control module further comprises: an image display unit configured to display the white light images, the first near-infrared window fluorescent images, the second near-infrared window fluorescent images, the CT images, the second near-infrared window three-dimensional and tomographic images and the first near-infrared window three-dimensional and tomographic images;

the image display unit is communicatively connected with the signal control unit, the data reading unit, the image processing unit, and the three-dimensional reconstruction unit, respectively.

The second aspect of the embodiment of the present disclosure discloses a second near-infrared window/first near-infrared window dual-mode fluorescence tomography method, which is applied to any of the second near-infrared window/first near-infrared window dual-mode fluorescence tomography systems mentioned above, the second near-infrared window/first near-infrared window dual-mode fluorescence tomography method reconstructs second near-infrared window three-dimensional and tomographic images and first near-infrared window three-dimensional and tomographic images based on Gaussian weighted neighborhood fused Lasso regularization.

Specifically, referring to FIG. 5, the method applied to the above system may include the following steps:

Step S100: the white light emitting device is turned on, and control signals are output, by the signal control unit of the central control module, to a first near-infrared window collection camera and a second near-infrared window collection camera to cause the cameras to collect the white light images;

Step S200: the white light emitting device is turned off, the laser is turned on to output the excitation light, and control signals are output, by the signal control unit of the central control module, to the first near-infrared window camera and the second near-infrared window camera to cause the cameras to collect the fluorescent images;

Step S300: the laser is turned off, and a control signal is output, by the signal control unit of the central control module, to the CT imaging module to collect the CT images;

Step S400: de-noising and enhancing pre-process is performed, by the image processing unit of the central control module, on the white light images, the fluorescent images, and the CT images collected in steps S100, S200 and S300;

Step S500: the fluorescent images are registered, by the three-dimensional reconstruction unit of the central control module, to the CT images according to the white light images, the three-dimensional images of the tumor in the body of the mouse are obtained by combining the fluorescence distribution, light intensities and other information, and the second near-infrared window/first near-infrared window dual-mode fluorescence tomography reconstruction is completed.

In step S500, the spatial structure information and the two-dimensional images of the surface of the imaging object collected by the system need to be combined with the propagation characteristics of near-infrared fluorescence photons in biological tissues to establish a mapping relationship between the internal light sources and surface fluorescence, and then the three-dimensional spatial distribution of the internal light sources is deduced based on the reconstruction algorithm.

The reconstruction method used is a new light source tomography reconstruction method. It makes use of the local correlation between nodes to construct a correlation matrix and adds it to the regular term of the optimization function. The optimization function used is $$f(x)=\tfrac{1}{2}\|A^S X-\Phi_m^S\|^2+\lambda_1\|X\|_1+\lambda_2\|L_C X\|_1$$

Wherein, $L_C$ is correlation matrix which is defined as follows:

$$L_C = (-l_{p,q})_{n\times n}$$

$$l_{p,q} = \begin{cases} -\Sigma_{r\neq p} l_{p,r} & p = q \\ w_{p,j} & q \text{ is the } j\text{-nearest neighbor of } q \\ 0 & \text{otherwise} \end{cases}$$

This problem is an improved fusing Lasso problem. Traditional gradient optimization methods do not applicable again, so it needs to be solved by using the Split Bregman iterative algorithm.

Those skilled in the art may clearly understand that, for the convenience and conciseness of description, the specific working process and related descriptions of the system described above may refer to the corresponding processes in the foregoing method embodiments, and will not be repeated herein.

It should be noted that the system provided in the foregoing embodiment is only illustrated by the division of the above functional modules. In practical applications, the above functions may be assigned to different function modules according to needs, that is, the modules or steps in the embodiments of the present disclosure may be decomposed or combined again. For example, the modules in the above embodiments may be combined into one module or further divided into multiple sub-modules to complete all or part of the functions described above. The names of the modules and steps involved in the embodiments of the present disclosure are only used to distinguish each module or step, which are not regarded as improper restrictions to the present disclosure.

Those skilled in the art may clearly understand that, for the convenience and conciseness of description, the specific working process and related descriptions of the storage device and processing device described above may refer to the corresponding processes in the foregoing method embodiments, and will not be repeated herein.

Those skilled in the art should be able to realize that the modules and method steps of each example described in combination with the embodiments disclosed herein may be implemented by electronic hardware, computer software, or a combination thereof, and the programs corresponding to the software modules and method steps may be placed in a random access memory (RAM), a memory, a read-only memory (ROM), an electrically programmable ROM, an electrically erasable programmable ROM, registers, a hard disk, a removable disk, a CD-ROM, or any other form of storage medium well known in the technical field. In order to clearly illustrate the interchangeability of electronic hardware and software, the composition and steps of each example have been described generally in terms of functions in the above description. Whether these functions are performed by electronic hardware or software depends on the specific application and design constraints of the technical solution. Those skilled in the art may use different methods to implement the described functions for each specific application, but such implementation should not be considered to be beyond the scope of the present disclosure.

The term "comprising" or any other similar term is intended to encompass non-exclusive inclusion such that a process, method, article, or device/apparatus comprising a series of elements includes not only those elements, but also other elements not explicitly listed, or elements that are inherent to these processes, methods, articles, or device/apparatuses are also included.

So far, the technical solution of the present disclosure has been described with reference to the preferred embodiments shown in the accompanying drawings. However, it will be easily understood by those skilled in the art that the scope of protection of the present disclosure is obviously not limited to these specific embodiments. Without departing from the principle of the present disclosure, those skilled in the art may make equivalent changes or replacements to related technical features, and the technical solutions after these changes or replacements will fall into the protection scope of the present disclosure.

We claim:

1. A second near-infrared window/first near-infrared window dual mode fluorescence tomography system, comprising:
   a lighting module configured to irradiate a mouse with a white light and collect white light images, wherein the lighting module comprises a white light emitting device configured to emit the white light, and the white light emitting device has an adjustable luminous intensity;
   an excitation module configured to irradiate a tumor region of the mouse with a second near-infrared window excitation light and a first near-infrared window excitation light such that fluorescent dye in the tumor region emits fluorescence, wherein the excitation module comprises a laser configured to emit the second near-infrared window excitation light and the first near-infrared window excitation light with tunable wavelengths;
   a first near-infrared window collection module configured to collect first near-infrared window white light images and first near-infrared window fluorescent images formed by the fluorescence emitted by the fluorescent dye in the tumor region, wherein the first near-infrared window collection module comprises a first near-infrared window camera configured to collect the first near-infrared window fluorescent images and the first near-infrared window white light images;
   a second near-infrared window collection module configured to collect second near-infrared window white light images and second near-infrared window fluorescent images formed by the fluorescence emitted by the fluorescent dye in the tumor region wherein the second near-infrared window collection module comprises a second near-infrared window camera configured to collect the second near-infrared window fluorescent images and the second near-infrared window white light images;
   a CT imaging module configured to irradiate the mouse and generate CT images for the mouse; and
   a central control module configured to reconstruct second near-infrared window three-dimensional and tomographic images and first near-infrared window three-dimensional and tomographic images based on the second near-infrared window white light images, the first near-infrared window white light images, the second near-infrared window fluorescent images, the first near-infrared window fluorescent images, and the CT images, wherein
      the second near-infrared window white light images and the first near-infrared window white light images are respectively used to register the second near-infrared window fluorescent images to the CT images and to register the first near-infrared window fluorescent images to the CT images;
      the second near-infrared window fluorescent images are used to reconstruct a second near-infrared window fluorescent light source distribution in a body of the mouse; and
      the first near-infrared window fluorescent images are used to reconstruct a first near-infrared window fluorescent light source distribution in the body of the mouse;
   wherein the central control module is configured to:
      after the white light emitting device is turned on, output control signals to the first near-infrared window camera and the second near-infrared window camera to cause the first near-infrared window camera and the second near-infrared window camera to collect the first near-infrared window white light images and the second near-infrared window white light images, respectively;
      after the white light emitting device is turned off and the laser is turned on to output the excitation light, output control signals to the first near-infrared window camera and the second near-infrared window camera to cause the first near-infrared window camera and the second near-infrared window camera to collect the first near-infrared window fluorescent images and the second near-infrared window fluorescent images, respectively;
      after the laser is turned off, output a control signal to the CT imaging module to collect the CT images;
      performing de-noising and enhancing pre-process on the collected first near-infrared window white light images, the collected second near-infrared window white light images, the collected first near-infrared window fluorescent images, the collected second near-infrared window fluorescent images, and the collected CT images; and
      registering the first near-infrared window fluorescent images and the second near-infrared window fluorescent images to the CT images respectively according to the first near-infrared window white light images and the second near-infrared window white light images, obtaining the three-dimensional images of the tumor in the body of the mouse by combining the second near-infrared window fluorescent light source distribution and the first near-infrared window fluorescent light source distribution, so as to achieve the second near-infrared window/first near-infrared window dual-mode fluorescence tomography reconstruction, and wherein the system further comprises a rack, a turntable, and a mobile station, wherein:

the rack comprises a first base and a second base, the turntable is mounted on the second base of the rack in a manner capable of rotating in a vertical plane, the turntable is configured to fix the lighting module, the excitation module, the second near-infrared window collection module, the first near-infrared window collection module and the CT imaging module, and a rotation of the turntable is driven by a power mechanism communicatively connected with the central control module; and the mobile station is configured to fix the mouse, the mouse is fixed to the mobile station by a mouse bed, the mobile station is movable in both a horizontal direction and a vertical direction, the mobile station comprises a vertical mobile station and a horizontal mobile station, the vertical mobile station is mounted on the horizontal mobile station in a manner capable of sliding in the vertical direction, and the horizontal mobile station is mounted, by parallel guides, on the first base of the rack in a manner capable of sliding in the horizontal direction.

2. The second near-infrared window/first near-infrared window dual-mode fluorescence tomography system according to claim 1, wherein the lighting module further comprises a white light conducting device and a white light beam expanding device, which are sequentially connected in an optical path, wherein the white light conducting device is configured to conduct a white light signal emitted by the white light emitting device to an imaging range of the mouse; and the white light beam expanding device is disposed near the imaging range, and the white light beam expanding device is configured to expand the white light to be irradiated to the mouse to produce a uniform lighting effect.

3. The second near-infrared window/first near-infrared window dual-mode fluorescence tomography system according to claim 1, wherein the excitation module further comprises an adapter device, an excitation light conducting device, and an excitation light beam expanding device, which are sequentially connected in an optical path, wherein the excitation light conducting device is configured to conduct the excitation lights;

the adapter device is configured to conduct the excitation lights emitted by the laser to the excitation light conducting device; and the excitation light beam expanding device is configured to diverge the excitation lights.

4. The second near-infrared window/first near-infrared window dual-mode fluorescence tomography system according to claim 1, wherein the central control module comprises:

a signal control unit configured to control the lighting module, the excitation module, the second near-infrared window collection module, the first near-infrared window collection module, and the CT imaging module, respectively;

a data reading unit configured to read the second near-infrared window white light images, the first near-infrared window white light images the second near-infrared window fluorescent images, the first near-infrared window fluorescent images, and the CT images;

an image processing unit configured to pre-process the second near-infrared window white light images, the first near-infrared window white light images the second near-infrared window fluorescent images, the first near-infrared window fluorescent images, and the CT images; and a three-dimensional reconstruction unit configured to register the second near-infrared window fluorescent images to the CT images and register the first near-infrared window fluorescent images to the CT images according to the second near-infrared window white light images and the first near-infrared window white light images respectively, and combine the second near-infrared window fluorescent light source distribution, the first near-infrared window fluorescent light source distribution, intensities of the second near-infrared window white light images, intensities of the first near-infrared window white light images of the intensities of the second near-infrared window fluorescent images, and intensities of the first near-infrared window fluorescent images to obtain the second near-infrared window three-dimensional and tomographic images and the first near-infrared window three-dimensional and tomographic images of the tumor region within the body of the mouse.

5. The second near-infrared window/first near-infrared window dual-mode fluorescence tomography system according to claim 4, wherein the central control module further comprises:

an image display unit configured to display the second near-infrared window white light images, the first near-infrared window white light images the first near-infrared window fluorescent images, the second near-infrared window fluorescent images, the CT images, the second near-infrared window three-dimensional and tomographic images, and the first near-infrared window three-dimensional and tomographic images; and the image display unit is communicatively connected with the signal control unit, the data reading unit, the image processing unit, and the three-dimensional reconstruction unit, respectively.

6. A second near-infrared window/first near-infrared window dual-mode fluorescence tomography method, applied to a second near-infrared window/first near-infrared window dual-mode fluorescence tomography system, wherein the second near-infrared window/first near-infrared window dual-mode fluorescence tomography system comprises:

a lighting module configured to irradiate a mouse with a white light and collect white light images, wherein the lighting module comprises a white light emitting device configured to emit the white light, and the white light emitting device has an adjustable luminous intensity;

an excitation module configured to irradiate a tumor region of the mouse with a second near-infrared window excitation light and a first near-infrared window excitation light such that fluorescent dye in the tumor region emits fluorescence, wherein the excitation module comprises a laser configured to emit the second near-infrared window excitation light and the first near-infrared window excitation light with tunable wavelengths;

a first near-infrared window collection module configured to collect first near-infrared window white light images and first near-infrared window fluorescent images formed by the fluorescence emitted by the fluorescent dye in the tumor region, wherein the first near-infrared window collection module comprises a first near-infrared window camera configured to collect the first near-infrared window fluorescent images and the first near-infrared window white light images;

a second near-infrared window collection module configured to collect second near-infrared window white light images and second near-infrared window fluorescent images formed by the fluorescence emitted by the fluorescent dye in the tumor region, wherein the second near-infrared window collection module comprises a second near-infrared window camera configured to collect the second near-infrared window fluorescent images and the second near-infrared window white light images;

a CT imaging module configured to irradiate the mouse and generate CT images for the mouse; and a central control module configured to reconstruct second near-infrared window three-dimensional and tomographic images and first near-infrared window three-dimensional and tomographic images based on the second near-infrared window white light images, the first near-infrared window white light images, the second near-infrared window fluorescent images, the first near-infrared window fluorescent images, and the CT images, wherein the second near-infrared window white light images and the first near-infrared window white light images are respectively used to register the second near-infrared window fluorescent images to the CT images and to register the first near-infrared window fluorescent images to the CT images;

the second near-infrared window fluorescent images are used to reconstruct a second near-infrared window fluorescent light source distribution in a body of the mouse; and the first near-infrared window fluorescent images are used to reconstruct a first near-infrared window fluorescent light source distribution in the body of the mouse;

wherein the central control module is configured to:

after the white light emitting device is turned on, output control signals to the first near-infrared window camera and the second near-infrared window camera to cause the first near-infrared window camera and the second near-infrared window camera to collect the first near-infrared window white light images and the second near-infrared window white light images, respectively;

after the white light emitting device is turned off and the laser is turned on to output the excitation light, output control signals to the first near-infrared window camera and the second near-infrared window camera to cause the first near-infrared window camera and the second near-infrared window camera to collect the first near-infrared window fluorescent images and the second near-infrared window fluorescent images, respectively;

after the laser is turned off, output a control signal to the CT imaging module to collect the CT images;

performing de-noising and enhancing pre-process on the collected first near-infrared window white light images, the collected second near-infrared window white light images, the collected first near-infrared window fluorescent images, the collected second near-infrared window fluorescent images, and the collected CT images; and registering the first near-infrared window fluorescent images and the second near-infrared window fluorescent images to the CT images respectively according to the first near-infrared window white light images and the second near-infrared window white light images, obtaining the three-dimensional images of the tumor in the body of the mouse by combining the second near-infrared window fluorescent light source distribution and the first near-infrared window fluorescent light source distribution, so as to achieve the second near-infrared window/first near-infrared window dual-mode fluorescence tomography reconstruction;

wherein the system further comprises a rack, a turntable, and a mobile station, wherein:

the rack comprises a first base and a second base, the turntable is mounted on the second base of the rack in a manner capable of rotating in a vertical plane, the turntable is configured to fix the lighting module, the excitation module, the second near-infrared window collection module, the first near-infrared window collection module and the CT imaging module, and a rotation of the turntable is driven by a power mechanism communicatively connected with the central control module; and the mobile station is configured to fix the mouse, the mouse is fixed to the mobile station by a mouse bed, the mobile station is movable in both a horizontal direction and a vertical direction, the mobile station comprises a vertical mobile station and a horizontal mobile station, the vertical mobile station is mounted on the horizontal mobile station in a manner capable of sliding in the vertical direction, and the horizontal mobile station is mounted, by parallel guides, on the first base of the rack in a manner capable of sliding in the horizontal direction; and wherein the second near-infrared window/first near-infrared window dual-mode fluorescence tomography method reconstructs second near-infrared window three-dimensional and tomographic images and first near-infrared window three-dimensional and tomographic images based on Gaussian weighted neighborhood fused Lasso regularization.

* * * * *